United States Patent
Seim et al.

(10) Patent No.: US 6,895,273 B2
(45) Date of Patent: May 17, 2005

(54) TEMPORARY TACHYARRHYTHMIA THERAPY MODES FOR ELECTROPHYSIOLOGIC TESTING

(75) Inventors: Gary Seim, Minneapolis, MN (US); Victor Chen, Minnetrista, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 495 days.

(21) Appl. No.: 09/827,771

(22) Filed: Apr. 6, 2001

(65) Prior Publication Data

US 2002/0147473 A1 Oct. 10, 2002

(51) Int. Cl.[7] .............................................. A61N 1/18
(52) U.S. Cl. ................................................ 607/14; 607/9
(58) Field of Search ................................ 607/14, 9, 11, 607/15, 16, 30

(56) References Cited

U.S. PATENT DOCUMENTS

| | | | | |
|---|---|---|---|---|
| 4,253,466 A | | 3/1981 | Hartlaub et al. ............... 607/30 |
| 5,213,098 A | * | 5/1993 | Bennett et al. ................ 607/18 |
| 5,540,725 A | * | 7/1996 | Bornzin et al. ................ 607/9 |
| 5,836,989 A | * | 11/1998 | Shelton ........................ 607/27 |
| 5,873,895 A | * | 2/1999 | Sholder et al. ................ 607/9 |
| 5,873,897 A | * | 2/1999 | Armstrong et al. ........... 607/14 |
| 6,058,328 A | * | 5/2000 | Levine et al. ................. 607/14 |
| 6,122,546 A | * | 9/2000 | Sholder et al. ................ 607/9 |

* cited by examiner

Primary Examiner—Daniel Robinson
(74) Attorney, Agent, or Firm—Crawford Maunu PLLC

(57) ABSTRACT

Systems and methods implemented with an implantable medical device (IMD) are provided for performing cardiac testing while temporarily disabling all or selected antitachyarrhythmia therapy delivery capabilities of the device. An initiation signal indicative of initiation of a cardiac test, such as an electrophysiologic test, is received by the IMD. In response to the test initiation signal, a capability of delivering tachyarrhythmia therapy to a chamber of the heart is temporarily disabled. While the capability of delivering tachyarrhythmia therapy is disabled, the subject heart chamber is monitored in response to electrophysiologic testing. The capability of delivering tachyarrhythmia therapy is automatically re-enabled to ensure availability of tachyarrhythmia therapy after completion or interruption of the electrophysiologic test.

32 Claims, 8 Drawing Sheets

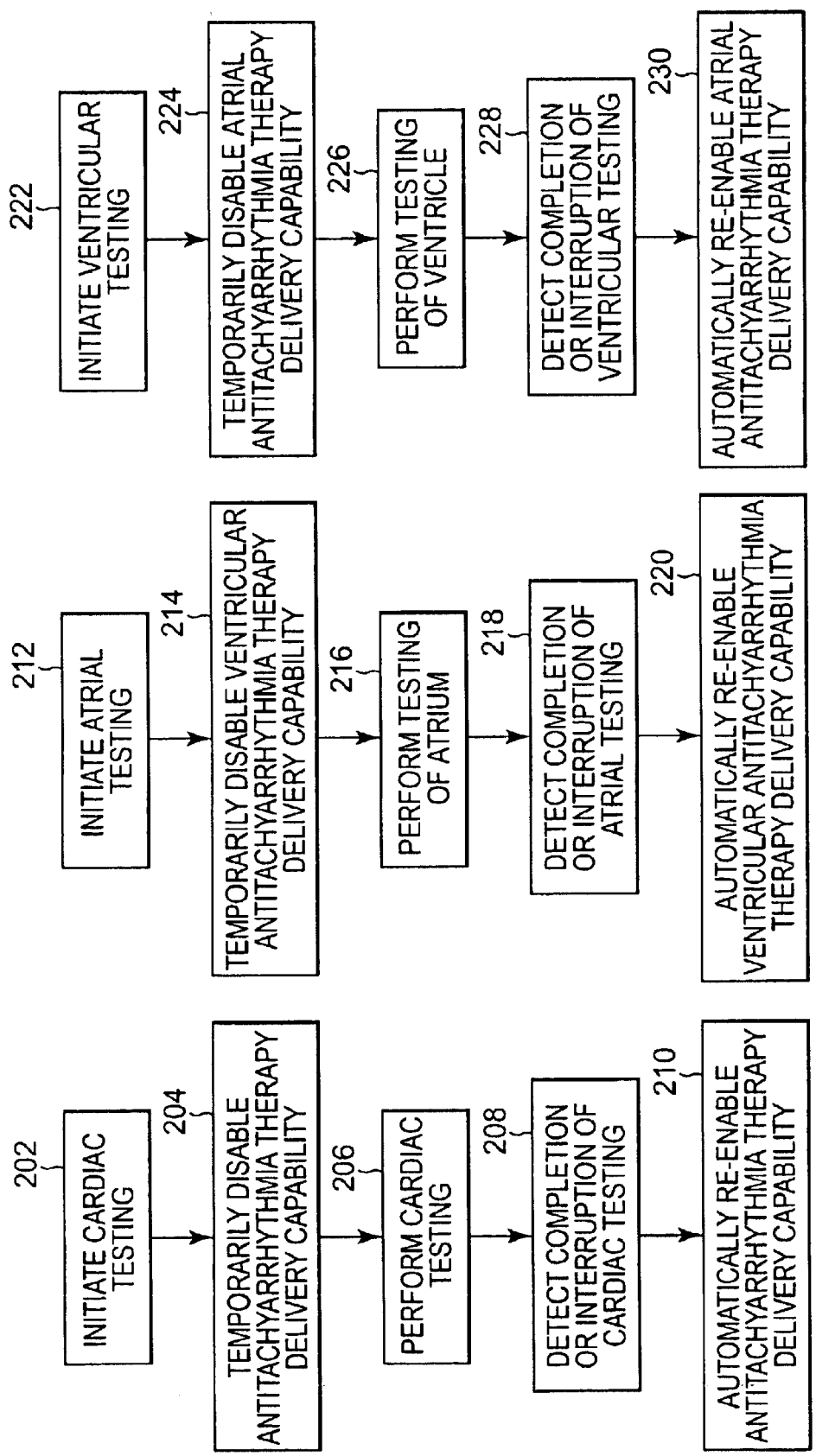

TEMPORARY TACHYARRHYTHMIA THERAPY MODES FOR ELECTROPHYSIOLOGIC TESTING

FIELD OF THE INVENTION

The present invention relates generally to implantable medical devices and, more particularly, to implantable pacemakers and cardioverter-defibrillators that can be programmed to operate in several tachyarrhythmia therapy modes during device implant and testing, such as during electrophysiologic testing.

BACKGROUND OF THE INVENTION

Implantable cardioverter-defibrillators (ICDs) have been developed that employ detection algorithms capable of recognizing and treating ventricular tachycardias and ventricular fibrillation. Detection algorithms are also being developed to recognize and treat atrial tachycardias and atrial fibrillation. In general, ICDs are designed to treat such tachycardias with antitachycardia pacing and low-energy cardioversion shocks in conjunction with back-up defibrillation therapy. These ICDs monitor the heart rate and the onset of the arrhythmia by sensing endocardial signals and determining when the heart is in need of either cardioversion to treat a given tachycardia or of defibrillation to treat a fibrillation condition.

Certain ICDs have been designed with dual chamber sensing capabilities to detect and analyze both ventricular and atrial endocardial signals. This increase in cardiac signal input to the ICD has provided an opportunity to determine the origin and the nature of atrial and ventricular tachyarrhythmia, and to reduce the frequency of inappropriate therapy being delivered to an implant patient.

Under certain conditions and testing, it may be desirable to temporarily disable, or otherwise alter, the normal antitachyarrhythmia detection and response programming of an ICD, such as during ICD implant, for example. It is imperative that any antitachyarrhythmia detection and response programming that is temporarily altered for purposes of conducting certain cardiac testing be returned to nominal operating condition at the conclusion of such testing.

For the reasons stated above, and for other reasons stated below which will become apparent to those skilled in the art upon reading the present specification, there is a need in the art for improved cardiac testing techniques, particularly during device implant, that provide for the alteration of standard atrial and ventricular arrhythmia detection and response programming of the device. There exists a further need for such techniques that provide failsafe assurance that any antitachyarrhythmia therapy programming that is altered for a particular cardiac test be returned to nominal operation condition at the conclusion of such testing. The present invention fulfills these and other needs, and provides advantages over prior art implementations.

SUMMARY OF THE INVENTION

The present invention is directed to systems and methods implemented with an implantable medical device (IMD) for performing cardiac testing while temporarily disabling all or selected antitachyarrhythmia therapy delivery capabilities of the device. According to an embodiment of the present invention, an initiation signal indicative of initiation of a cardiac test, such as an electrophysiologic test, is received by the IMD. In response to the test initiation signal, a capability of delivering tachyarrhythmia therapy to a chamber of the heart is temporarily disabled. While the capability of delivering tachyarrhythmia therapy is disabled, the subject heart chamber is monitored in response to electrophysiologic testing. The capability of delivering tachyarrhythmia therapy is automatically re-enabled to ensure availability of tachyarrhythmia therapy after completion or interruption of the electrophysiologic test.

According to one approach, the capability of delivering tachyarrhythmia therapy is automatically re-enabled in response to a loss of communication between the implantable medical device and an electrophysiologic tester during or after the electrophysiologic test. According to another approach, automatic re-enabling of the IMD's capability to deliver tachyarrhythmia therapy occurs in response to the IMD detecting intermittent communication between the IMD and the electrophysiologic tester during or after completion or interruption of the electrophysiologic test.

According to a further approach, the tachyarrhythmia therapy delivery capabilities of the IMD are automatically re-enabled in response to detection of a degraded communication link established between the IMD and the electrophysiologic tester during or after completion or interruption of the electrophysiologic test. The tachyarrhythmia therapy delivery capabilities of the IMD may also be temporarily disabled and subsequently re-enabled in response to command signals received from an external programmer, with automatic re-enablement being made available as a failsafe backup capability.

According to a further embodiment, automatic re-enabling of the tachyarrhythmia therapy delivery capabilities of the IMD may be suspended for a pre-programmed duration of time after detecting loss of, or disruption to, the communication link established between the IMD and the electrophysiologic tester. For example, the physician may select a duration of time (e.g., up to one hour) during which the tachyarrhythmia therapy delivery capabilities of the IMD remain disabled, irrespective of the status of the communication link between the IMD and electrophysiologic tester. Upon expiration of the physician selected time duration, the tachyarrhythmia therapy delivery capabilities of the IMD are automatically re-enabled.

In accordance with another embodiment, the capability of delivering tachyarrhythmia therapy is automatically re-enabled in response to expiration of a first time duration. The first time duration may range between about 30 seconds and about 1 hour. According to a further embodiment, the first time duration may be extended by a second time duration in response to a time extension signal. The second time duration is generally shorter than the first time duration.

A warning signal may be generated and communicated to the physician indicating imminent expiration of the first or an extended time duration. The physician may, in response to the warning signal, extend the first duration by selecting a desired extended time duration.

The initiation signal may be representative of a manually induced initiation signal, such as an initiation signal resulting from a physician's actions. The initiation signal may alternatively be representative of a signal generated by an electrophysiologic tester in response to a test algorithm or software programming, where the electrophysiologic tester is in communication with the implantable medical device. The initiation signal may, for example, include a monitor only signal, and disabling the antitachyarrhythmia therapy delivering capability of the IMD may involve switching modes from a monitoring with tachyarrhythmia therapy mode to a monitoring only mode.

In accordance with another embodiment of the present invention, an initiation signal indicative of initiation of a cardiac test is received. In response to this signal, a capability of delivering ventricular tachyarrhythmia therapy to a ventricule of a heart is disabled on a temporary basis. While the capability of delivering ventricular tachyarrhythmia therapy is disabled, induction pulses are delivered to an atrium of the heart during the cardiac test. After delivering induction pulses to the atrium, the atrium is monitored during the time in which the capability of delivering ventricular tachyarrhythmia therapy is temporarily disabled. The capability of delivering ventricular tachyarrhythmia therapy is automatically re-enabled to ensure availability of ventricular tachyarrhythmia therapy after completion or interruption of the cardiac test.

According to yet another embodiment, a body implantable system that implements methodologies of the present invention includes a transceiver for maintaining a telemetry link with an external cardiac tester. The system further includes a lead system comprising atrial and ventricular electrodes, and a detector, coupled to the lead system, that detects atrial and ventricular activity.

The system also includes a tachyarrhythmia therapy delivery unit and a controller. The controller, in response to receiving an initiation signal indicative of initiation of a cardiac test, disables a capability of the tachyarrhythmia therapy delivery unit to deliver tachyarrhythmia therapy to a chamber of the heart. The controller automatically re-enables the capability of the tachyarrhythmia therapy delivery unit to deliver tachyarrhythmia therapy to ensure availability of tachyarrhythmia therapy after completion or interruption of the cardiac test.

A signal integrity circuit is coupled to the transceiver and the controller. The signal integrity circuit produces a loss of link signal in response to detecting loss of the telemetry link with the external cardiac tester during the cardiac test. In response to the loss of link signal, the controller automatically re-enables the capability of the tachyarrhythmia therapy delivery unit to deliver tachyarrhythmia therapy.

The signal integrity circuit may also produce an intermittent link signal in response to detecting intermittent communication with the external cardiac tester during the cardiac test. The signal integrity circuit may further produce a degraded link signal in response to detecting degradation of the telemetry link with the external cardiac tester during the cardiac test. The controller automatically re-enables the capability of the tachyarrhythmia therapy delivery unit to deliver tachyarrhythmia therapy in response to the intermittent link signal or the degraded link signal.

The system may additionally or alternatively include a timer circuit coupled to the controller. The timer circuit produces a timeout signal in response to expiration of a first time duration. The controller automatically re-enables the capability of the tachyarrhythmia therapy delivery unit to deliver tachyarrhythmia therapy in response to the timeout signal. The first time duration may be extended by a second time duration in response to a time extension signal received from the cardiac tester by the transceiver.

The body implantable system may further include a mode switch. The initiation signal, in this configuration, is generated by the mode switch in response to manual or automatic switching of the mode switch from a Monitor with Therapy mode to a Monitor Only mode. The initiation signal is typically received from a cardiac tester in communication with the body implantable system.

The above summary of the present invention is not intended to describe each embodiment or every implementation of the present invention. For example, the methodologies of the present invention may be employed during cardiac testing other than EP testing. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 3–5 are flow diagrams depicting various processes of temporary tachyarrhythmia therapy mode implementations according to three embodiments of the present invention;

Figure 1:
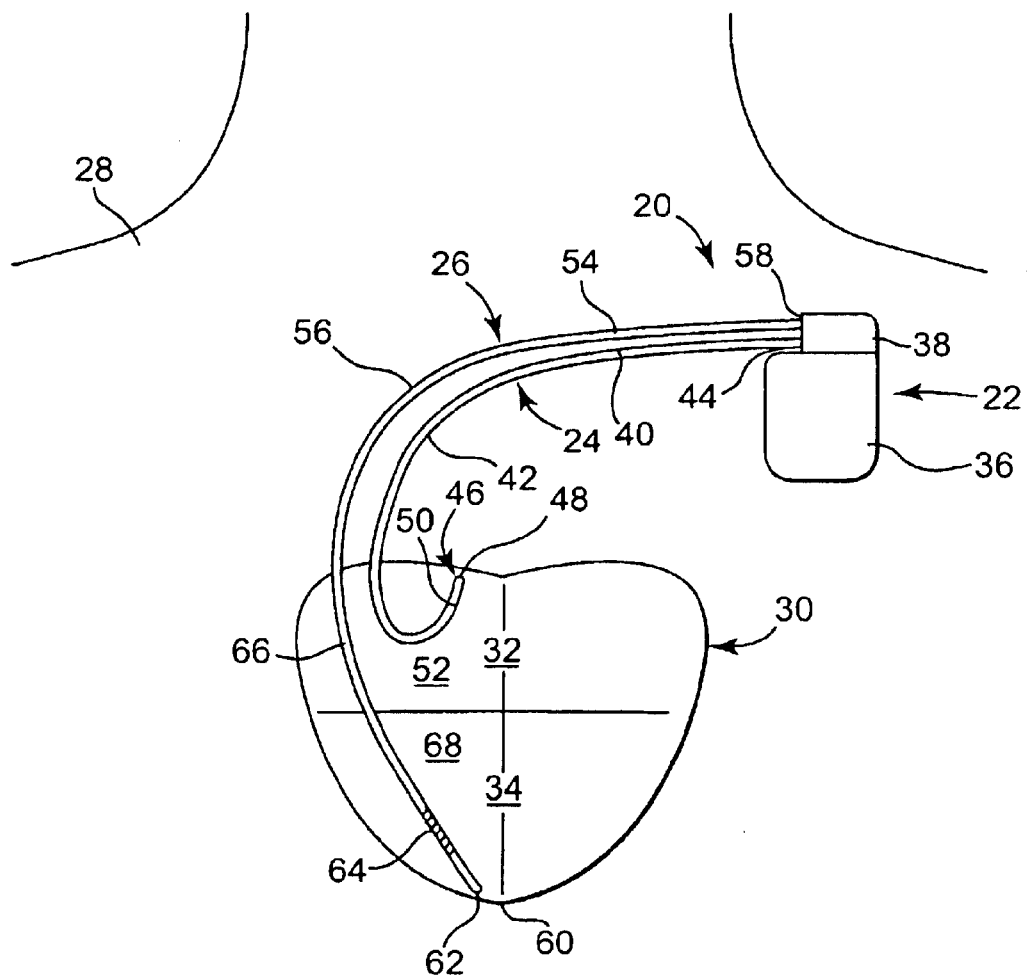
FIG. 1 is a depiction of an implantable medical device with which the temporary tachyarrhythmia therapy modes of the present invention may be practiced.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Referring now to the figures, and more particularly to FIG. 1, there is shown a body implantable system 20 that represents one of several types of systems with which the temporary tachyarrhythmia therapy modes of the present invention may be practiced. For example, the implantable pulse generator 22 may be representative of all or part of a pacemaker, defibrillator, cardioverter, cardiac monitor, or re-synchronization device. Accordingly, the temporary tachyarrhythmia therapy modes of the present invention may be practiced in a wide variety of implantable medical devices that provide cardiac sensing, pacing, and/or shocking capabilities.

The body implantable system 20 is shown to include an implantable pulse generator 22 coupled to an atrial lead 24 and a ventricular lead 26. The system 20 may also include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

The system 20, as shown in FIG. 1, is implanted in a human body 28 with portions of the atrial and ventricular leads 24 and 26 inserted into a heart 30 to detect and analyze electric cardiac signals produced by both the atria 32 and the ventricles 34 of the heart 30. The atrial and ventricular leads 24 and 26 also provide electrical energy to the heart 30 under certain predetermined conditions to treat various types of cardiac arrhythmia, including, for example, atrial and ventricular tachycardias, and atrial and ventricular fibrillation of the heart 30. The atrial and ventricular leads 24 and 26 also provide electrical energy to the heart 30 under certain predetermined cardiac testing procedures, such as during electrophysiologic testing, for example.

Figure 2:
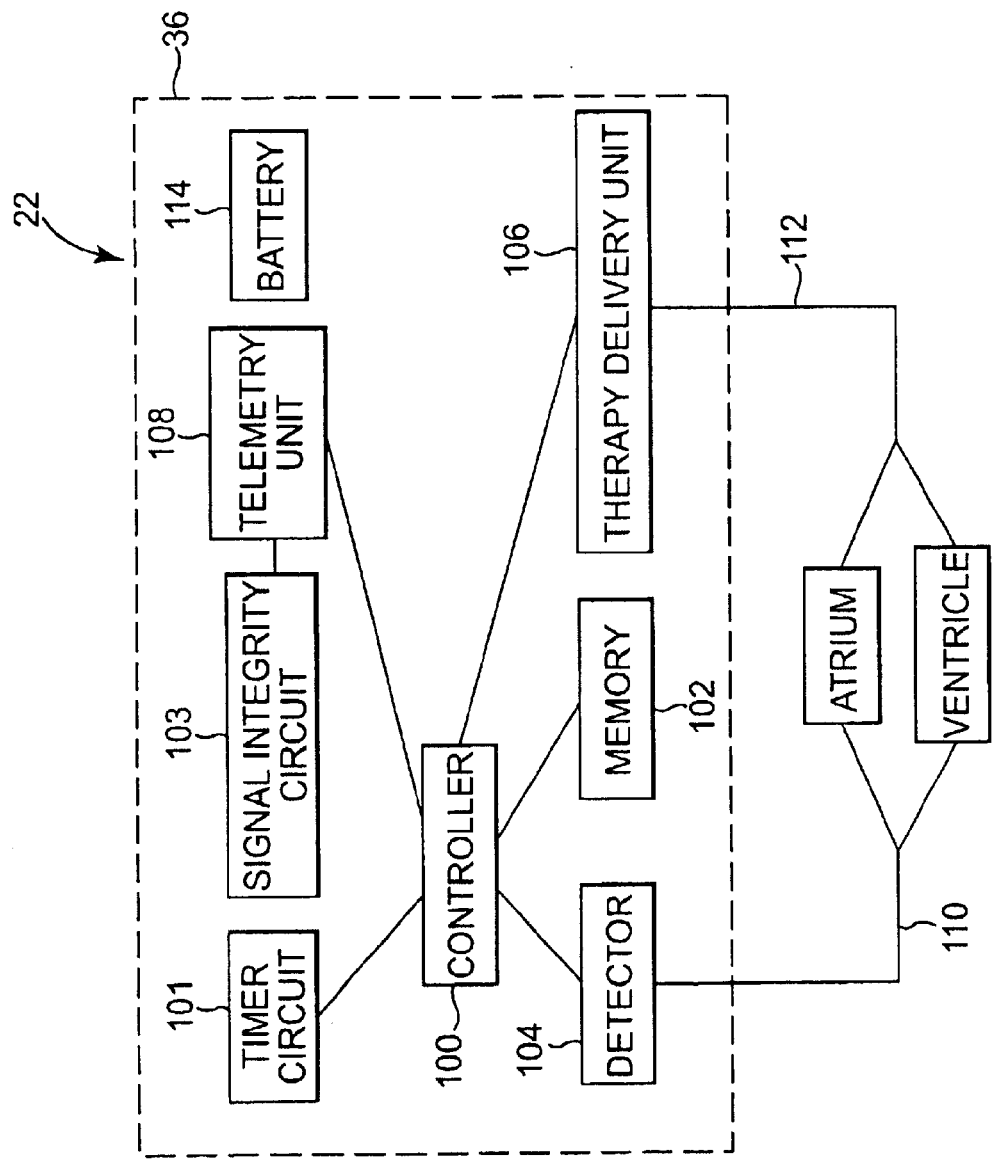
FIG. 2 is a block diagram of several components housed in the implantable medical device of FIG. 1.

A block diagram of the implantable pulse generator 22 electronics is provided in FIG. 2. The implantable pulse generator 22 includes a housing 36 which contains, among other components, a controller 100 and memory 102, which typically includes read only memory (ROM) and random access memory (RAM). Pulse generator 22 further includes a detector 104, which includes atrial and ventricular sense amplifiers (not shown), a therapy delivery unit 106, and a telemetry unit 108. The electronic components of the pulse generator 22 are interconnected by way of a bus connection (not shown).

Power to the implantable pulse generator 22 is supplied by an electrochemical battery 114 which is contained within the implantable pulse generator housing 36. The implantable pulse generator 22 is interrogated and programmed via bi-directional radio frequency telemetry through cooperative operation between the telemetry unit 108 and an external programmer in a manner known in the art. In the context of various embodiments of the present invention, the external programmer communicates electrophysiologic (EP) test signals and commands to the implantable pulse generator 22 during EP testing via a telemetry link established and maintained between the telemetry unit 108 and the external programmer. Monitoring data generated as part of EP testing is communicated from the telemetry unit 108 of the implantable pulse generator 22 to the external programmer via the telemetry link for evaluation by the physician.

The implantable pulse generator 22 is shown to further include a signal integrity circuit 103 coupled to the telemetry unit 108. The signal integrity circuit 103 analyzes the telemetry link established and maintained between the telemetry unit 108 and the external programmer. In one embodiment, the signal integrity circuit 103 analyzes the telemetry link to detect loss of the telemetry link during or following EP testing. In another embodiment, the signal integrity circuit 103 analyzes the telemetry link to determine if the telemetry link becomes intermittent or the integrity of the link degrades below an acceptable level during or following EP testing.

The implantable pulse generator 22 may also include a timer circuit 101. The timer circuit, according to one embodiment, is programmed to initiate a timeout duration upon deactivation of antitachyarrhythmia therapies during EP testing. The timer circuit 101 may be set to expire after a predetermined timeout duration. The timeout duration is typically set to a period of time deemed necessary for safely conducting EP testing while the antitachyarrhythmia therapy delivery capabilities of the IMD are temporarily disabled. The timeout duration may also represent a time period selected by the physician, which may include a duration of time before and/or after EP testing, in which the antitachyarrhythmia therapy delivery capabilities of the IMD are temporarily disabled.

The temporary tachyarrhythmia therapy modes implemented by system 20 are embodied in one or more algorithms as firmware within memory 102, and are executed by the controller 100. The detector 104 is also connected to the controller 100, and contains a plurality of electrical connections 110 coupled to the atrial and ventricular sense amplifiers. The outputs of the sense amplifiers are connected to the controller 100, such that atrial and ventricular signals received through the detector 104 are analyzed by the algorithms implemented within the controller 100. The controller 100 is also coupled to the therapy delivery unit 106, which controls the delivery of electrical energy to the heart 30 through a plurality of electrical output connections 112 to affect the sinus rhythm of the heart 30 under certain combinations of atrial 32 and ventricular 34 conditions. The controller 100 also controls the therapy delivery unit 106 to deliver EP test signals or other induction scheme signals to the heart 30, typically in response to commands received from an external programmer, through electrical output connections 112.

Referring again to FIG. 1, a connector block 38 is mounted on the implantable pulse generator 22. The connector block 38 has two connector ports for coupling the atrial lead 24 and the ventricular lead 26 to the detector 104 and the therapy delivery unit 106 of the implantable pulse generator 22. Additional connector ports can be added to the connector block 38, as in the case of configurations having three or more ports as is known in the art. Alternatively, the connector block 38 can be provided with one connector port for coupling an implantable transvenous lead to the implantable pulse generator 22. It is understood that atrial and ventricular sensing and pacing/defibrillating functions may be accomplished using a single lead system employing atrial and ventricular conductors/electrodes, rather than by use of the dual lead system shown in FIG. 1.

In general, the electrical activity in the heart 30 is sensed, and therapies are delivered to the heart 30, through at least one transvenous pacing/defibrillation lead connected to the implantable pulse generator 22. Unipolar and/or bipolar pacing and sensing electrodes can be used in conjunction with the transvenous pacing/defibrillation lead. In the embodiment shown in FIG. 1, bipolar leads and sensing circuits are utilized for sensing both the atrial 32 and the ventricular 34 activity. Sensing atrial activity includes the determination of atrial P-waves for purposes of determining atrial intervals. Ventricular activity is monitored by sensing for the occurrence of ventricular R-waves for purposes of determining ventricular intervals. Pacing therapies to the atrium 32 or ventricle 34 are delivered to the heart 30 using these same leads.

The system 20 may also employ defibrillation electrodes which are connected to the electrical output connections 112, and serve to deliver cardioversion and defibrillation level electrical pulses to the heart 30 as determined by the programming of controller 100. The housing 36 of the system 20 may be used as an optional defibrillation electrode, where the housing 36 of the implantable pulse generator 22 is electrically connected to a cathode pole of the therapy delivery unit 106. All defibrillation electrical pulses are delivered to the heart with at least two defibrillation electrodes, or through at least one defibrillation electrode and the housing 36 of the implantable pulse generator 22. The system 20 supports a plurality of pacing regimens.

In addition to the lead configuration shown in FIG. 1, the system 20 supports several other lead configurations and types. For example, it is possible to use ventricular epicardial rate sensing, atrial endocardial bipolar pace/sensing, ventricular endocardial bipolar pace/sensing, epicardial patches, and ancillary leads in conjunction with the implantable pulse generator 22.

In the embodiment of system 20 depicted in FIG. 1, the atrial lead 24 has an elongated body 40 having a peripheral surface 42, proximal and distal ends, 44 and 46, a first atrial electrode 48, and a second atrial electrode 50 on the peripheral surface 42. The first atrial electrode 48 and the second atrial electrode 50 receive bipolar electrical cardiac signals from the right atrium chamber 52 of the heart 30, and are attached on the peripheral surface 42 of the elongated body 40.

The first atrial electrode 48 is situated at or adjacent to the distal end 46 of the elongated body 40 and is either a pacing tip electrode or a semi-annular or annular electrode partially or completely encircling the peripheral surface 42 of the elongated body 40. The second electrode 50 is an annular or semi-annular electrode encircling or partially encircling the peripheral surface 42 of the elongated body 40. The second electrode 50 is spaced longitudinally along the peripheral surface 40 from the first atrial electrode 48 and the distal end 46 of the atrial lead 24, such that when the atrial lead 24 is inserted into the right atrial chamber 52 of the heart 30, the first atrial electrode 48 is in physical contact with a portion of a wall of the right atrial chamber 52 of the heart 30 and the second electrode 50 is within the right atrium chamber 52.

Electrical conductors extend longitudinally within the elongated body 40 of the atrial lead 24 from a connection end at the proximal end 44 and make connection to the first and second atrial electrodes 48 and 50. The proximal end 44 of the atrial pacing lead 24 is attached to the connector block 38 of the implantable pulse generator 22. The connector block 38 provides electrical coupling between the contact ends of the electrical conductors of atrial lead 24 with the atrial sense amplifier of the detector 104 and the therapy delivery unit 106, such that the implantable pulse generator 22 receives bipolar signals from, and delivers bipolar pacing to, the right atrium 52 of the heart 30.

The ventricular lead 26 includes an elongated body 54 having a peripheral surface 56, proximal and distal ends, 58 and 60, and a ventricle pacing electrode 62. The ventricular lead 26 also includes a first defibrillation electrode 64 and a second defibrillation electrode 66 situated on the peripheral surface 56 of the elongated body 54. The ventricular pacing electrode 62 and the first defibrillation electrode 64 are adapted to receive electrical cardiac signals from the right ventricle chamber 68 of the heart 30, and are attached on the peripheral surface of the elongated body 54. The second defibrillation electrode 66 is spaced apart and longitudinally on the peripheral surface 56 of the ventricular lead 26. This configuration affords positioning of the ventricular lead 26 in the heart 30 with the ventricular pacing electrode 62 in the apex of the right ventricle 68, the first defibrillation electrode 64 within the right ventricle chamber of the heart, and the second defibrillation electrode 66 within the right atrium chamber 52 or a major vein leading to right atrium.

Electrical leads extend longitudinally within the elongated body 54 of the ventricular lead 26 from a connection end at the proximal end 58 to make connection with the ventricular pacing electrode 62, the first defibrillation electrode 64, and the second defibrillation electrode 66. The proximal end 58 of the ventricular lead 26 is attached to the connector block 38 of the implantable pulse generator 22. The connector block 38 provides for electrical coupling between the contact ends of the electrical conductors of ventricular lead 26 with the ventricular sense amplifier of the detector 104 and the therapy delivery unit 106, such that the implantable pulse generator 22 receives either unipolar or bipolar signals from, and can deliver unipolar or bipolar pacing to, the right ventricle 68 and defibrillation electrical pulses to the ventricles 34 of the heart 30.

The atrial lead 24 and the ventricular lead 26 are releasably attached to, and are separated from, the implantable pulse generator 22 to facilitate insertion of the atrial lead 24 into the heart 30. The proximal end 44 of the atrial lead 24 and the proximal end 58 of the ventricular lead 26 are adapted to seal together with the connector ports of the implantable pulse generator 22 to thereby engage the contact ends of the atrial lead 24 and the ventricular lead 26 with the plurality of electrical connections 110 and the therapy delivery unit 106 of the implantable pulse generator 22. The implantable pulse generator 22 of the system 20 is then positioned subcutaneously within the body 26.

Referring now to FIG. 3, there is shown in flow diagram form several processes involving employment of temporary tachyarrhythmia therapy modes during testing of the heart, such as testing that occurs during an IMD implant operation or other operation involving the IMD. For certain cardiac tests, such as electrophysiologic tests (EP tests), for example, it is necessary or desirable to temporarily deactivate certain antitachyarrhythmia therapies that can be delivered by the IMD during such tests.

Electrophysiologic testing of the heart during IMD implant surgery or other cardiac procedure typically involves purposefully inducing arrhythmias through delivery of rapid pacing induction energy to the heart according to a rapid pacing induction scheme. After delivering the induction scheme energy to the heart, the response of the IMD is monitored during EP testing to ensure that the IMD is properly detecting and responding to the induced arrhythmias. During EP testing of a first chamber of the heart, it may be undesirable to allow the antitachyarrhythmia therapies associated with a second heart chamber to interfere with the EP tests performed on the first chamber. In this case, the antitachyarrhythmia therapies associated with the second heart chamber may be temporarily disabled.

For example, an IMD can be programmed to provide both atrial and ventricular antitachyarrhythmia therapies. In such devices, backup ventricular antitachyarrhythmia therapy is made available during delivery of atrial antitachyarrhythmia therapies under normal operating conditions. Backup ventricular antitachyarrhythmia therapy is made available in order to ensure than any unintended ventricular arrhythmic episode that may occur during application of the atrial antitachyarrhythmia therapy is detected and properly responded to by the IMD.

During EP testing of such an IMD during implant, for example, it may be desirable to temporarily disable ventricular antitachyarrhythmia therapies while induction tests are performed on the right atrium. It is noted that ventricular monitoring functions are typically operative immediately following delivery of induction energy to the right atrium and for the duration of time in which ventricular antitachyarrhythmia therapies are temporarily disabled.

By way of further example, atrial antitachyarrhythmia therapies may be temporarily disabled while induction tests are performed on the right ventricle. During the time in which atrial antitachyarrhythmia therapies are temporarily disabled, and after delivering induction energy to the right ventricle, atrial monitoring functions are typically operative.

It is imperative that the antitachyarrhythmia therapies temporarily disabled for purposes of conducting EP or other cardiac testing be enabled at the conclusion of such testing. For example, an IMD may provide for multiple operating modes that can be selectively switched, either manually or electronically, during EP testing. Such an IMD may be switched from a Monitor with Therapy mode, in which antitachyarrhythmia therapy delivery is enabled, to Monitor Only mode, in which antitachyarrhythmia therapy delivery is disabled, in order to perform or enhance EP testing.

At the conclusion of EP testing, the physician must ensure that the IMD is switched from the Monitor Only mode to the Monitor with Therapy mode before the patient is permitted to leave the testing facility. Otherwise, the antitachyarrhythmia therapy delivery capability of the patient's IMD will not be enabled. As such, the IMD will not be capable of responding to a detected arrhythmic condition, which can have adverse or catastrophic consequences.

There have been instances in which the antitachyarrhythmia therapy delivery capability of an IMD has not been properly re-enabled after conclusion of EP testing. Such failures to reactivate the antitachyarrhythmia therapy delivery capabilities of the IMD are often a result of physician or assistant oversight. Although a number of solutions have been proposed to reduce the human error factor in this situation, such proposed solutions still require some degree of human participation or intervention.

In contrast to such proposed approaches, the temporary tachyarrhythmia therapy modes of the present invention provide for failsafe assurance that antitachyarrhythmia therapy delivery is properly re-enabled at the conclusion of EP testing. Moreover, the temporary tachyarrhythmia therapy modes of the present invention provide for failsafe assurance that antitachyarrhythmia therapy delivery is properly re-enabled in response to certain conditions that may arise during EP testing. Accordingly, the human error factor associated with prior proposed solutions is eliminated by employment of the methodologies of the present invention.

Turning now to FIG. 3, there is illustrated several processes associated with a temporary tachyarrhythmia therapy mode implementation in accordance with an embodiment of the present invention. According to a typical operating scenario, a cardiac test, such as an EP test, for example, is initiated 202. Initiation 202 of the cardiac test may be accomplished manually or electronically. Manual initiation of the cardiac test is typically accomplished by setting a mode switch of the EP tester (e.g., external programmer) to the appropriate setting by the presiding physician. Electronic initiation of the cardiac test may be accomplished by software commands transmitted from the EP tester to the IMD. The software commands cause the IMD to operate in a cardiac test mode, such as an EP test mode.

In response to the cardiac test initiation signal, the IMD temporarily disables 204 antitachyarrhythmia therapy delivery to all or prescribed portions of the heart. Cardiac testing is performed 206 in accordance with the selected test procedure during the time in which antitachyarrhythmia therapy delivery is temporarily disabled. Completion or interruption of cardiac testing is advantageously detected 208 in-situ by the IMD.

Upon detecting 208 completion or interruption of cardiac testing by the IMD, the temporarily disabled antitachyarrhythmia therapy delivery function is re-enabled 210 to ensure the availability of such antitachyarrhythmia therapy or therapies after completion or interruption of cardiac testing. In-situ detection of cardiac test completion or interruption by the IMD advantageously provides for failsafe re-enabling of the IMD's antitachyarrhythmia therapy delivery capability and eliminates the human error factor associated with prior art methodologies discussed hereinabove.

FIG. 4 illustrates several processes associated with a temporary tachyarrhythmia therapy mode implementation in accordance with another embodiment of the present invention. According to this embodiment, a cardiac test, such as an EP test associated with the atria, is initiated 212. In response to initiating atrial testing, the IMD temporarily disables 214 the ventricular antitachyarrhythmia therapy delivery capability of the IMD. Selected atrial testing is performed 216 during the time in which ventricular antitachyarrhythmia therapy delivery is temporarily disabled. Upon detecting 218 completion or interruption of atrial testing by the IMD, the temporarily disabled ventricular antitachyarrhythmia therapy delivery function is re-enabled 220 to ensure the availability of such ventricular antitachyarrhythmia therapy after the patient is released from the physician's care.

FIG. 5 illustrates several processes associated with a temporary tachyarrhythmia therapy mode implementation in accordance with a further embodiment of the present invention. According to this embodiment, a ventricular test, such as an EP test associated with the ventricles, is initiated 222. In response to initiating ventricular testing, the IMD temporarily disables 224 the atrial antitachyarrhythmia therapy delivery capability of the IMD. Selected ventricular testing is performed 226 during the time in which atrial antitachyarrhythmia therapy delivery is temporarily disabled. Upon detecting 228 completion or interruption of ventricular testing by the IMD, the temporarily disabled atrial antitachyarrhythmia therapy delivery function is re-enabled 230 to ensure the availability of such atrial antitachyarrhythmia therapy after the patient is released from the physician's care.

Figure 6:
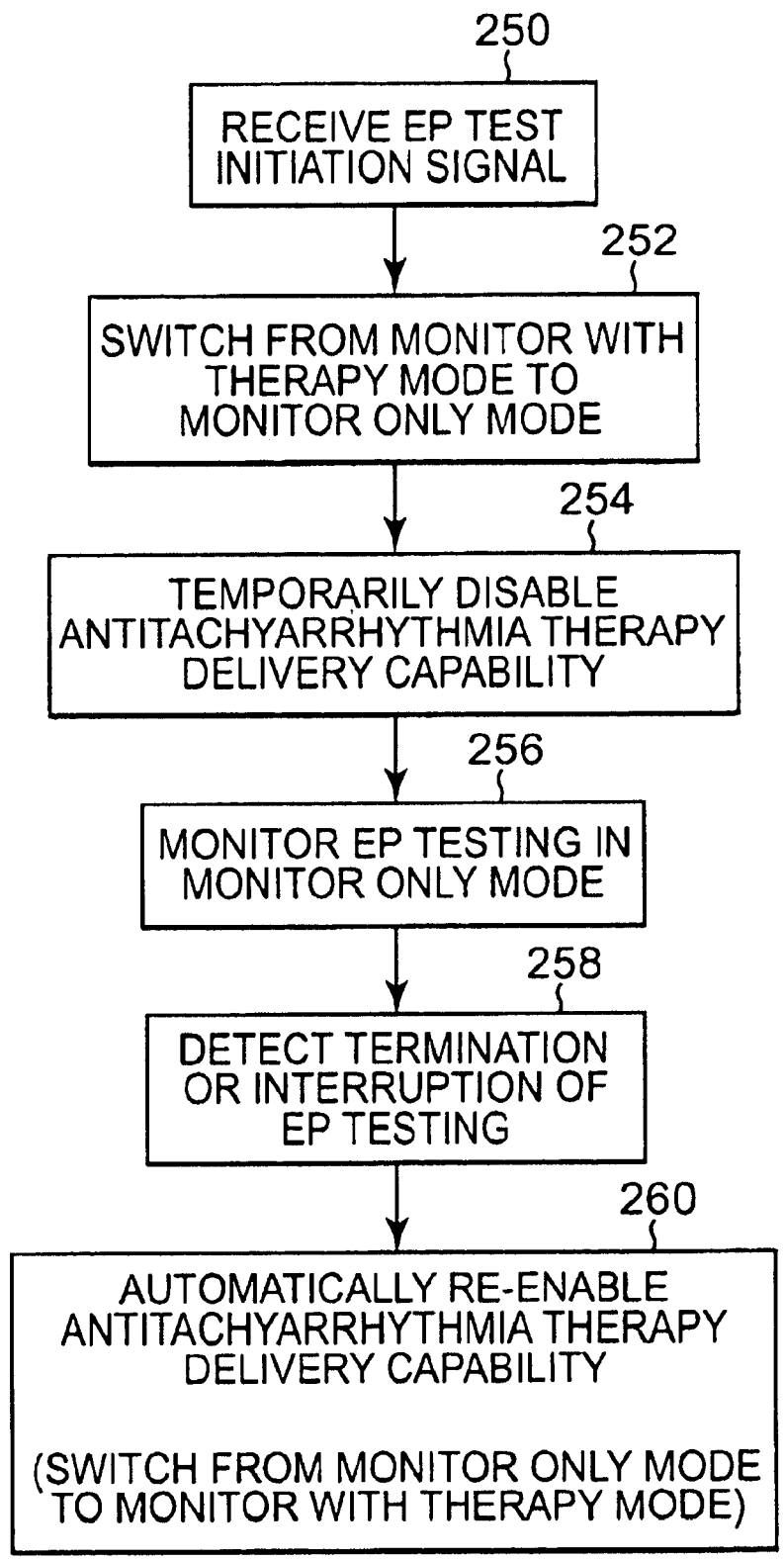
FIG. 6 is a flow diagram depicting various processes of a temporary tachyarrhythmia therapy mode implementation according to another embodiment of the present invention.

In accordance with one embodiment, and as depicted in FIG. 6, an IMD that is programmed to implement temporary tachyarrhythmia therapy modes of the present invention can be switched to selectively operate in a Monitor with Therapy mode and a Monitor Only mode, among other modes. As discussed previously, the Monitor with Therapy mode provides for antitachyarrhythmia therapy delivery, while the Monitor Only mode provides disablement of antitachyarrhythmia therapy delivery. In the following illustrative example, it is assumed that an EP test is to be performed during IMD implant surgery or other surgery involving the IMD, it being understood that such cardiac testing may be performed on a follow-up basis.

An EP test initiation signal is received 250 by the IMD. As was discussed previously, the EP test initiation signal may be generated manually by the physician or electronically by programming instructions embedded in the EP test software and transmitted in the form of telemetry signals from the EP tester to the IMD. In response to the EP test initiation signal, the IMD switches 252 from a Monitor with Therapy mode to a Monitor Only mode. As a result of this mode switching, all or selected antitachyarrhythmia therapy delivery capabilities of the IMD are temporarily disabled 254. The IMD, while operating in Monitor Only mode, monitors 256 cardiac activity in response to EP testing of the heart. The IMD detects 258 termination or interruption of EP testing, and responds to such detection by automatically re-enabling 260 the antitachyarrhythmia therapy delivery capabilities of the IMD.

Figure 7:
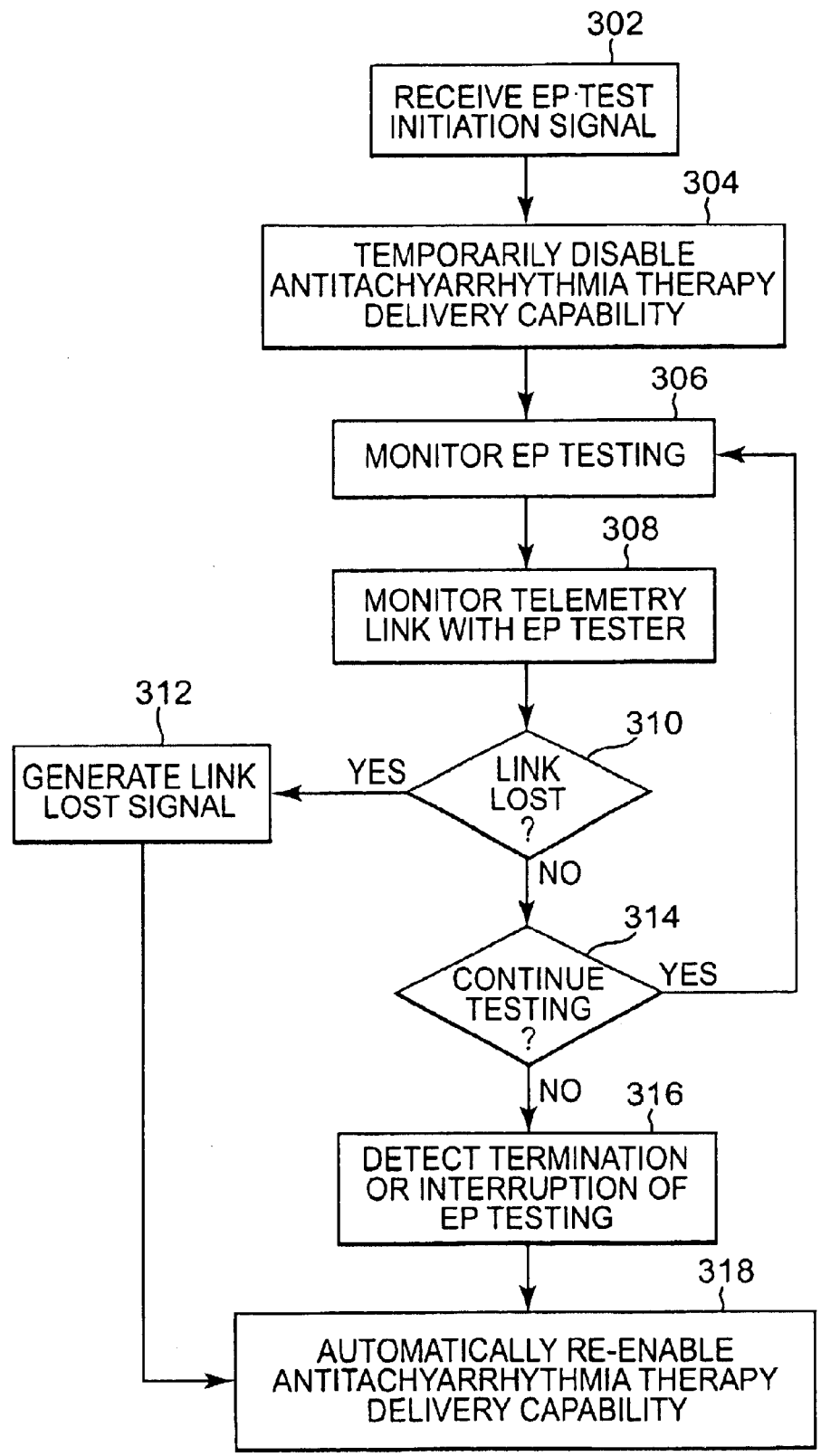
FIGS. 7–8 are flow diagrams depicting various processes of temporary tachyarrhythmia therapy mode implementations that employ telemetry link monitoring according to two embodiments of the present invention.

According to another embodiment of the present invention, and as shown in FIG. 7, an EP test initiation signal is received 302 and, in response to such signal, antitachyarrhythmia therapy delivery capabilities of the IMD are temporarily disabled 304. The IMD monitors 306 cardiac activity in response to EP testing of the heart, which typically includes transmitting monitoring data to the external programmer for evaluation by the presiding physician. According to this embodiment, the telemetry link established between the IMD and the external EP tester or programmer is monitored 308 by the IMD.

In particular, the IMD monitors the telemetry link to ensure that the link is maintained during the EP test procedure. If the IMD detects 310 that the telemetry link has been terminated, either purposefully or unintentionally, a link lost signal is generated 312, typically by the telemetry unit 108 shown in FIG. 2. In response to the link lost signal, the IMD autonomously (i.e., without assistance from the external programmer or other external manual or electronic resource) re-enables 318 the antitachyarrhythmia therapy delivery capabilities of the IMD.

While the telemetry link is maintained between the IMD and external programmer, EP testing continues 314 until such time as the IMD is instructed by the programmer to terminate the EP test or the IMD detects a prolonged and unintended interruption during EP testing. Upon detecting 316 termination or interruption of EP testing, the IMD automatically re-enables 318 the antitachyarrhythmia therapy delivery capabilities of the IMD.

Figure 8:
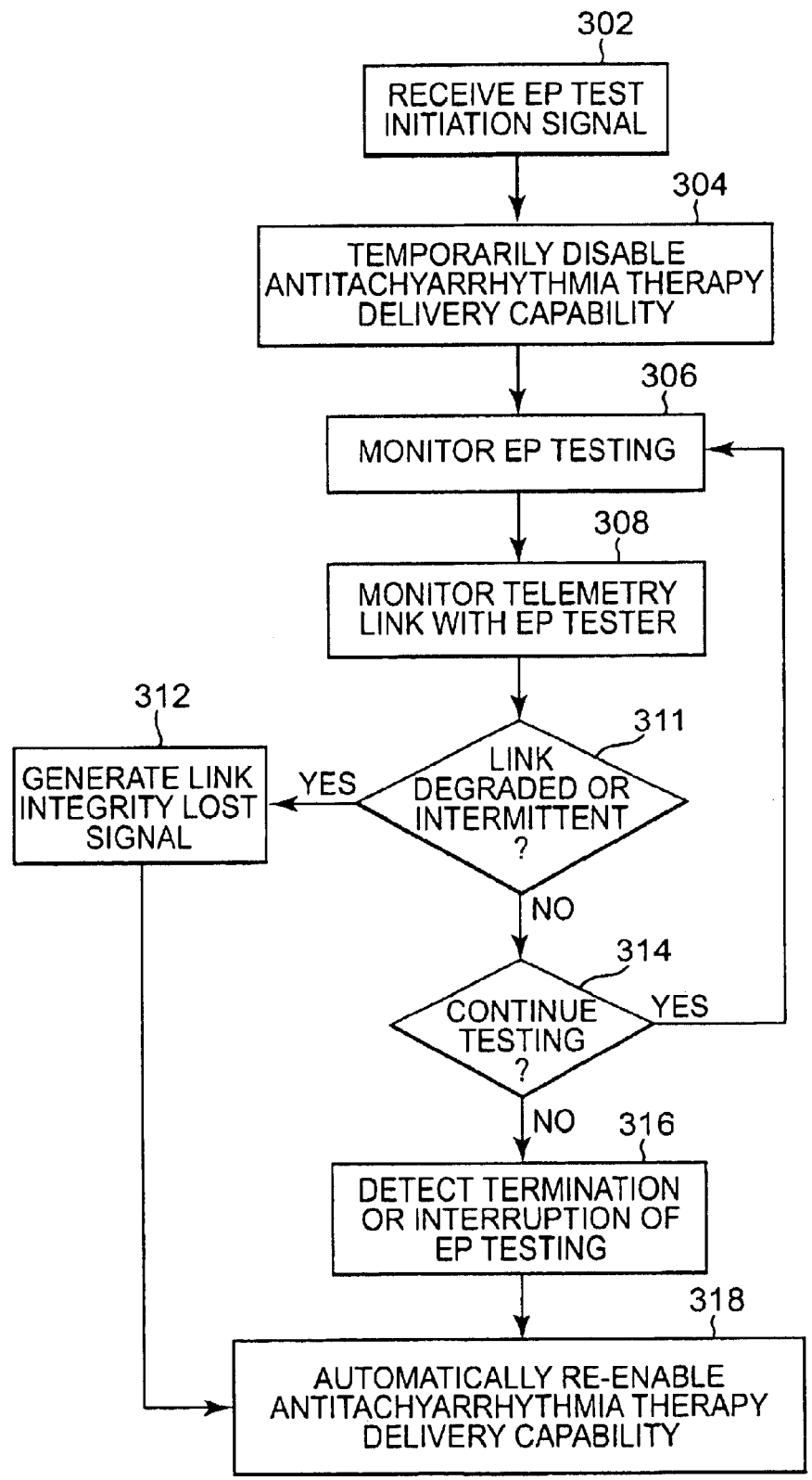

FIG. 8 illustrates another methodology by which the integrity of the telemetry link established and maintained between the IMD and external programmer is evaluated by the IMD. According to this approach, an EP test initiation signal is received 302, antitachyarrhythmia therapy delivery is temporarily disabled 304, and cardiac activity is monitored 306 in response to EP testing of the heart. According to this embodiment, the integrity or quality of the telemetry link established between the IMD and the external EP tester or programmer is monitored 308 by the IMD.

The IMD monitors the telemetry link to determine if the communication link established between the IMD and external programmer is intermittent or the link becomes degraded to an unacceptable level. If the IMD detects 311 that the telemetry link has become unacceptably intermittent or degraded, a link integrity lost signal is generated 312 and, in response to such signal, the IMD autonomously re-enables 318 the antitachyarrhythmia therapy delivery capabilities of the IMD. Otherwise, EP testing continues 314 until such time as the IMD is instructed by the programmer to terminate the EP test or the IMD detects a prolonged and unintended interruption during EP testing. The IMD automatically re-enables 318 the antitachyarrhythmia therapy delivery capabilities of the IMD upon detecting 316 termination or interruption of EP testing.

The IMD can detect a loss of communication or unacceptable degradation or intermittency of the telemetry link established between the IMD and external programmer using several techniques. For example, the IMD can detect a loss of the telemetry link by detecting a violation of the operative communication protocol, such as by a violation of a handshaking protocol. The IMD can also detect a loss of the telemetry link by expiration of a transmission timer due to the failure to receive data from the external programmer within a predefined time period. This data may take the form of programming instructions or other signals that are typically communicated between the external programmer and the IMD, or may take the form of a link verification signal repeatedly transmitted between the IMD and programmer to ensure continuity of the telemetry link.

The IMD may also detect intermittency of the telemetry link using a similar transmission timer and an additional counter. The counter may accumulate the number and duration of transmission intermittencies that occur during EP testing. If the number and/or durations of such intermittencies exceed preestablished limits, the IMD determines that the telemetry link is unacceptably unstable, and automatically re-enables the antitachyarrhythmia therapy delivery capabilities of the IMD. Other known techniques may be employed to determine if the telemetry link is intermittent to the extent that termination of the Monitor Only mode is warranted.

The quality of the telemetry signal can be determined by the IMD using several techniques. For example, the signal-to-noise ratio (SNR) of signals transmitted by the external programmer and received by the IMD may be monitored by the IMD. A bit error rate or bit fall-out rate may be also determined by the IMD. Other signal quality factors associated with the telemetry link may be evaluated by the IMD to determine the quality of the communication link established between the IMD and the external programmer.

Figure 9:
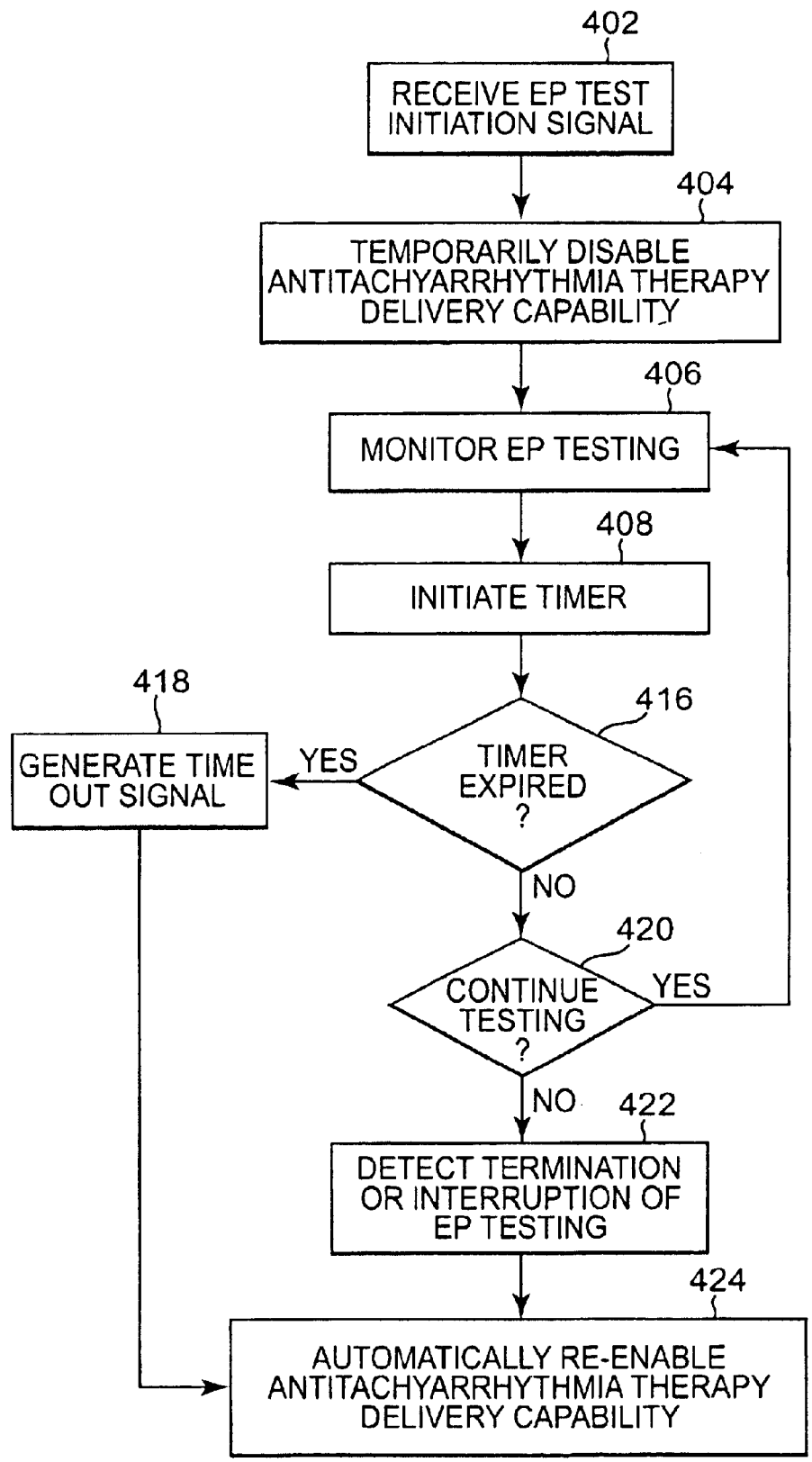
FIGS. 9–10 are flow diagrams depicting various processes of temporary tachyarrhythmia therapy mode implementations that employ timeout durations according to two additional embodiments of the present invention.

FIG. 9 illustrates another methodology by which antitachyarrhythmia therapy delivery capabilities of the IMD are automatically re-enabled according to a further embodiment of the present invention. An EP test initiation signal is received 402, antitachyarrhythmia therapy delivery is temporarily disabled 404, and cardiac activity is monitored 406 in response to EP testing of the heart. According to this embodiment, a timer is initiated 408 in response to disablement of the antitachyarrhythmia therapy delivery capabilities of the IMD. The timer may be set to expire after a predetermined timeout duration. The timeout duration is typically set to a period of time believed necessary for safely conducting EP testing or other cardiac testing/surgery while the antitachyarrhythmia therapy delivery capabilities of the IMD are temporarily disabled. As mentioned previously, the timeout duration may also represent a time period selected by the physician, which may include a duration of time before and/or after EP testing, in which the antitachyarrhythmia therapy delivery capabilities of the IMD are temporarily disabled. For example, the timeout duration may be set to between about 30 seconds and 1 hour.

In most cases, the timeout duration is sufficiently long to allow completion of EP testing under nominal conditions. If the timer expires 416, irrespective of whether EP testing has been concluded, a timeout signal is generated 418 and, in response to this signal, antitachyarrhythmia therapy delivery capabilities of the IMD are automatically re-enabled 424 by the IMD. According to this embodiment, automatic re-enabling of IMD antitachyarrhythmia therapy delivery upon expiration of the timer provides failsafe assurance that the antitachyarrhythmia therapy delivery capabilities of the IMD are made available for detecting and responding to tachyarrhythmic conditions after the patient is released from the physician's care.

If the timeout duration of the timer has not elapsed, EP testing continues 420 until such time as the IMD is instructed by the programmer to terminate the EP test or the IMD detects a prolonged and unintended interruption during EP testing. The IMD automatically re-enables 424 the antitachyarrhythmia therapy delivery capabilities of the IMD upon detecting termination or interruption of EP testing.

Figure 10:
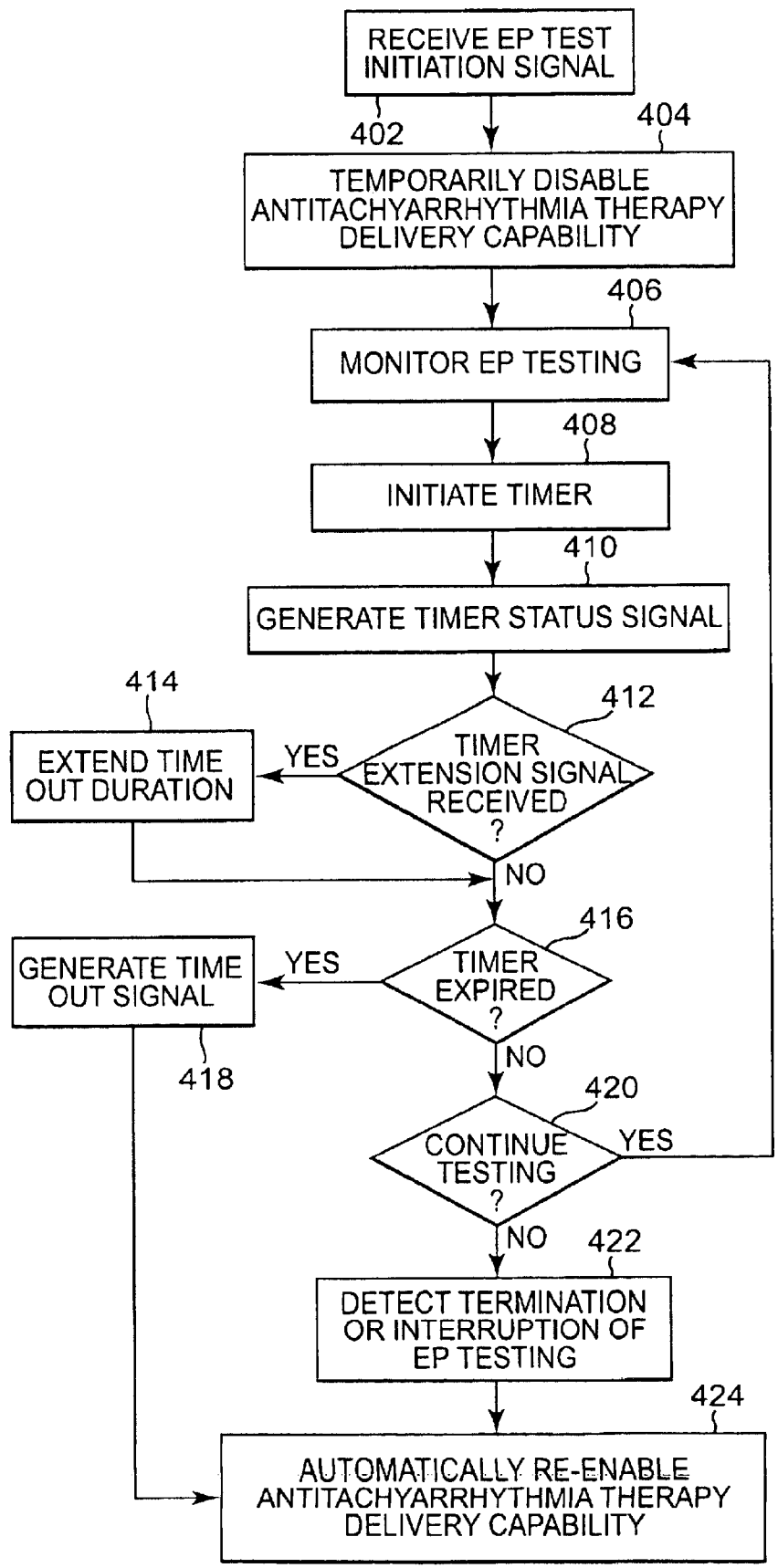

According to the embodiment depicted in FIG. 10, an EP test initiation signal is received 402, antitachyarrhythmia therapy delivery is temporarily disabled 404, and cardiac activity is monitored 406 in response to EP testing of the heart. A timer is initiated 408 in response to disablement of the antitachyarrhythmia therapy delivery capabilities of the IMD. The timer may be set to expire after a predetermined timeout duration, as in the case of the embodiment described previously with regard to FIG. 9.

In accordance with this embodiment, a timer status signal is generate 410 indicative of the current status of the timer. For example, the timer status signal may be representative of the allotted timeout duration and/or the amount of time remaining before the allotted timeout duration has elapsed. The timer status signal is communicated to the external programmer. The external programmer provides an visual or aural indication of the timer status information to the presiding physician.

Assuming that EP testing is progressing nominally, the physician may wish to extend the timer's timeout duration if conditions warrant such an extension. In this case, the physician may cause the external programmer to generate 410 a timer extension signal which is transmitted to the IMD. If a timer extension signal is received 412 by the IMD, and if the extension signal is received by the IMD prior to elapsing of the original timeout duration, the timeout duration of the timer is extended 414. The timer's timeout duration is typically extended by a period of time less than the original timeout duration, such as one half or less of the original timeout duration. This timer extension period may be selected by the physician or may be preprogrammed.

If the timer expires 416, after elapsing of the original timeout duration or the extended timeout duration, a timeout signal is generated 418 and, in response to this signal, antitachyarrhythmia therapy delivery capabilities of the IMD are automatically re-enabled 424 by the IMD. If the timeout duration of the timer has not elapsed, EP testing continues 420 until such time as the IMD is instructed by the programmer to terminate the EP test or the IMD detects a prolonged and unintended interruption during EP testing. The IMD automatically re-enables 424 the antitachyarrhythmia therapy delivery capabilities of the IMD upon detecting termination or interruption of EP testing.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method implemented with an implantable medical device, comprising:
   receiving an initiation signal indicative of initiation of an electrophysiologic test;
   disabling a capability of delivering tachyarrhythmia therapy to a chamber of the heart;
   monitoring, while the capability of delivering tachyarrhythmia therapy is disabled, the heart chamber in response to the electrophysiologic test; and
   automatically re-enabling the capability of delivering tachyarrhythmia therapy to ensure availability of tachyarrhythmia therapy after completion or interruption of the electrophysiologic test.

2. The method of claim 1, wherein automatically re-enabling further comprises automatically re-enabling the capability of delivering tachyarrhythmia in response to a loss of communication between the implantable medical device and an electrophysiologic tester during or after the electrophysiologic test.

3. The method of claim 1, wherein automatically re-enabling further comprises automatically re-enabling the capability of delivering tachyarrhythmia in response to intermittent communication between the implantable medical device and an electrophysiologic tester during or after completion or interruption of the electrophysiologic test.

4. The method of claim 1, wherein automatically re-enabling further comprises automatically re-enabling the capability of delivering tachyarrhythmia in response to degraded communication between the implantable medical device and an electrophysiologic tester during or after completion or interruption of the electrophysiologic test.

5. The method of claim 1, wherein automatically re-enabling further comprises automatically re-enabling the capability of delivering tachyarrhythmia in response to expiration of a first time duration.

6. The method of claim 5, wherein the first time duration ranges between about 30 seconds and about 1 hour.

7. The method of claim 5, wherein the first time duration is extended by a second time duration in response to a time extension signal.

8. The method of claim 7, wherein the second time duration is shorter than the first time duration.

9. The method of claim 1, wherein receiving the initiation signal comprises receiving a manually induced initiation signal.

10. The method of claim 1, wherein receiving the initiation signal comprises receiving the initiation signal generated by an electrophysiologic tester implementing an electrophysiologic test algorithm, the electrophysiologic tester being in communication with the implantable medical device.

11. The method of claim 1, wherein the initiation signal comprises a monitor only signal, and disabling the delivering capability comprises switching modes from a monitoring with tachyarrhythmia therapy mode to a monitoring only mode.

12. A method implemented with an implantable medical device, comprising:
   receiving an initiation signal indicative of initiation of a cardiac test;
   disabling a capability of delivering ventricular tachyarrhythmia therapy to a ventricle of a heart;
   delivering, while the capability of delivering ventricular tachyarrhythmia therapy is disabled, antitachycardia pacing to an atrium of the heart during the cardiac test;
   monitoring the atrium while the capability of delivering ventricular tachyarrhythmia therapy is disabled; and
   automatically re-enabling the capability of delivering ventricular tachyarrhythmia therapy to ensure availability of ventricular tachyarrhythmia therapy after completion or interruption of the cardiac test.

13. The method of claim 12, wherein automatically re-enabling further comprises automatically re-enabling the capability of delivering ventricular tachyarrhythmia in response to a loss of communication between the implantable medical device and a cardiac tester during or after the cardiac test.

14. The method of claim 12, wherein automatically re-enabling further comprises automatically re-enabling the capability of delivering ventricular tachyarrhythmia in response to intermittent communication between the implantable medical device and a cardiac tester during or after completion or interruption of the cardiac test.

15. The method of claim 12, wherein automatically re-enabling further comprises automatically re-enabling the capability of delivering ventricular tachyarrhythmia in response to degraded communication between the implantable medical device and a cardiac tester during or after completion or interruption of the cardiac test.

16. The method of claim 12, wherein automatically re-enabling further comprises automatically re-enabling the capability of delivering ventricular tachyarrhythmia in response to expiration of a first time duration.

17. The method of claim 16, wherein the first time duration ranges between about 30 second and about 1 hour.

18. The method of claim 16, wherein the first time duration is extended by a second time duration in response to a time extension signal.

19. The method of claim 18, wherein the second time duration is shorter than the first time duration.

20. The method of claim 12, wherein receiving the initiation signal comprises receiving a manually induced initiation signal.

21. The method of claim 12, wherein receiving the initiation signal comprises receiving the initiation signal from a cardiac tester in communication with the implantable medical device.

22. The method of claim 12, wherein the initiation signal comprises a monitor only signal, and disabling the delivering capability comprises switching modes from a monitoring with tachyarrhythmia therapy mode to a monitoring only mode.

23. A body implantable system, comprising:
    a transceiver for maintaining a telemetry link with an external cardiac tester;
    a lead system comprising atrial and ventricular electrodes;
    a detector, coupled to the lead system, that detects atrial and ventricular activity;
    a tachyarrhythmia therapy delivery unit and
    a controller, the controller, in response to receiving an initiation signal indicative of initiation of a cardiac test, disabling a capability of the tachyarrhythmia therapy delivery unit to deliver tachyarrhythmia therapy to a chamber of the heart, the controller automatically re-enabling the capability of the tachyarrhythmia therapy delivery unit to deliver tachyarrhythmia therapy to ensure availability of tachyarrhythmia therapy after completion or interruption of the cardiac test.

24. The system of claim 23, further comprising a signal integrity circuit coupled to the transceiver and the controller, the signal integrity circuit producing a loss of link signal in response to detecting loss of the telemetry link with the external cardiac tester during the cardiac test, the controller automatically re-enabling the capability of the tachyarrhythmia therapy delivery unit to deliver tachyarrhythmia therapy in response to the loss of link signal.

25. The system of claim 23, further comprising a signal integrity circuit coupled to the transceiver and the controller, the signal integrity circuit producing an intermittent link signal in response to detecting intermittency of the telemetry link with the external cardiac tester during the cardiac test, the controller automatically re-enabling the capability of the tachyarrhythmia therapy delivery unit to deliver tachyarrhythmia therapy in response to the intermittent link signal.

26. The system of claim 23, further comprising a signal integrity circuit coupled to the transceiver and the controller, the signal integrity circuit producing a degraded link signal in response to detecting degradation of the telemetry link with the external cardiac tester during the cardiac test, the controller automatically re-enabling the capability of the tachyarrhythmia therapy delivery unit to deliver tachyarrhythmia therapy in response to the degraded link signal.

27. The system of claim 23, further comprising a timer circuit coupled to the controller, the timer circuit producing a timeout signal in response to expiration of a first time duration, the controller automatically re-enabling the capability of the tachyarrhythmia therapy delivery unit to deliver tachyarrhythmia therapy in response to the timeout signal.

28. The system of claim 27, wherein the first time duration ranges between about 30 seconds and about 1 hour.

29. The system of claim 27, wherein the first time duration is extended by a second time duration in response to a time extension signal received from the cardiac tester by the transceiver.

30. The system of claim 29, wherein the second time duration is shorter than the first time duration.

31. The system of claim 23, wherein the body implantable system further comprises a mode switch, the initiation signal being generated by the mode switch in response to manual or automatic switching of the mode switch from a Monitor with Therapy mode to a Monitor Only mode.

32. The method of claim 1, wherein receiving the initiation signal comprises receiving the initiation signal from a cardiac tester in communication with the body implantable system.

* * * * *